United States Patent
Itoh (10) Patent No.: US 7,472,994 B2
(45) Date of Patent: Jan. 6, 2009

(54) OPHTHALMOLOGIC IMAGE PICKUP SYSTEM

(75) Inventor: Hiroshi Itoh, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 642 days.

(21) Appl. No.: 10/815,479

(22) Filed: Mar. 31, 2004

(65) Prior Publication Data

US 2004/0212780 A1    Oct. 28, 2004

(30) Foreign Application Priority Data

Apr. 25, 2003    (JP) ............................. 2003-121961

(51) Int. Cl.
 A61B 3/14    (2006.01)
 A61B 3/10    (2006.01)

(52) U.S. Cl. ...................... 351/206; 351/205

(58) Field of Classification Search ......... 351/205–207, 351/210
See application file for complete search history.

(56) References Cited

U.S. PATENT DOCUMENTS

| | | | | |
|---|---|---|---|---|
| 5,530,493 | A * | 6/1996 | Suzuki | 351/206 |
| 5,886,767 | A * | 3/1999 | Snook | 351/212 |
| 5,912,720 | A * | 6/1999 | Berger et al. | 351/206 |
| 6,190,011 | B1 * | 2/2001 | Fujieda | 351/206 |
| 6,325,511 | B1 | 12/2001 | Mizuochi | |
| 6,361,170 | B1 | 3/2002 | Bille | 351/221 |
| 6,736,507 | B2 * | 5/2004 | Kudryashov et al. | 351/206 |
| 2001/0028439 | A1 * | 10/2001 | Itoh | 351/206 |
| 2002/0036750 | A1 * | 3/2002 | Eberl et al. | 351/207 |
| 2002/0140825 | A1 | 10/2002 | Terashita | |
| 2003/0058349 | A1 | 3/2003 | Takemoto | |
| 2004/0156019 | A1 * | 8/2004 | Masaki | 351/206 |
| 2005/0094099 | A1 * | 5/2005 | Newman et al. | 351/205 |

FOREIGN PATENT DOCUMENTS

| | | |
|---|---|---|
| JP | 1987-211010 | 9/1987 |
| JP | 1987-211040 | 9/1987 |
| JP | 4-317629 | 11/1992 |
| JP | 1996-024222 | 1/1996 |
| JP | 09-206278 | 8/1997 |
| JP | 10-179523 | 7/1998 |
| JP | 2001-094714 | 4/2001 |
| JP | 2002-360521 | 12/2002 |

OTHER PUBLICATIONS

Patent Abstracts of Japan 2000-175869, Jun. 27, 2000.
Patent Abstracts of Japan 2001-094714, Apr. 6, 2001.
Patent Abstracts of Japan 8-154244, Jun. 11, 1996.
An English abstract of JP 08-024222 published on Jan. 30, 1996.

* cited by examiner

*Primary Examiner*—Scott J Sugarman
*Assistant Examiner*—Dawayne A Pinkney
(74) *Attorney, Agent, or Firm*—Morgan & Finnegan, LLP (57) ABSTRACT

With respect to image data generated by plural kinds of eye fundus cameras, device information used for image pickup is added to picked-up-image information, and different image processings such as image reverse and aperture synthesization are performed based on the added device information.

8 Claims, 6 Drawing Sheets

OPHTHALMOLOGIC IMAGE PICKUP SYSTEM

BACKGROUND OF THE INVENTION

1. Field of the Invention

The present invention mainly relates to an ophthalmologic image pickup system that performs image processing on images picked up by plural kinds of eye fundus cameras.

2. Related Background Art

Up to now, in an ophthalmologic apparatus such as an eye fundus camera that observes an eye fundus of an eye to be examined and picks up an image thereof or a slit lamp (slit lamp microscope) that observes an anterior segment of the eye and picks up an image thereof, a 35 mm-film or an instant camera is used as a recording member. In order to prevent an image reader from image-reading and diagnosing an eye to be image-picked-up in a state in which the top, the bottom, the right, and the left thereof are erroneously judged, an image pickup device is designed such that each film becomes the same composition.

On the other hand, in recent years, there has been proposed a system in which a CCD camera is connected and incorporated and a picked-up image of the eye to be examined is displayed on a screen and outputted to a recording device such as a magneto optical disk or a video printer. Therefore, according as digitization of the image progresses, image reverse, contrast adjustment, and light-and-dark adjustment are electronically performed on the picked-up image. Alternatively, a protrusion of an aperture mask provided in a silver-salt film so as to facilitate distinguishment of the eye to be image-picked-up is electronically synthesized.

According to an example disclosed in, for example, JP 10-179523 A, when the digital camera is connected with the ophthalmologic apparatus such as the eye fundus camera, the picked-up image is subjected to reverse processing and displayed. On the other hand, when it is not connected, the reverse processing is not performed.

According to a method disclosed in JP 07-124121 A, the shape of an aperture portion is stored as numerical data to reduce a necessary memory capacity.

Also, according to an apparatus that adds additional information to an electronic image and uses a resultant image, as disclosed in JP 2000-023918 A, information indicating whether or not an image is required to be stored during image pickup is inputted by an additional information input unit. After the completion of the image pickup, whether or not the image is deleted is determined based on the information inputted by the additional information input unit.

Further, when an image of the eye fundus of the eye to be examined is picked up by Fluorescein fundus angiography (hereinafter referred to as an "FAG image pickup") using the eye fundus camera, it originally becomes a greenish color image. In general, because of ease of image reading, the greenish color image is converted into a white-and-black image, and γ characteristic adjustment and contrast processing are performed thereon for diagnosis. In addition, even in Indocyanine green angiography (hereinafter referred to as an "ICG image pickup"), similarly, the γ characteristic adjustment and the contrast processing are performed for diagnosis in many cases.

However, in order to prevent an image reader from image-reading and diagnosing the eye to be image-picked-up in a state in which the top, the bottom, the right, and the left thereof are erroneously judged, not all kinds of current ophthalmologic apparatuses are designed such that each film becomes the same composition. For example, as regards the aperture mask as well, there are various apparatuses; some apparatuses include a member but other apparatuses do not include the member.

Therefore, in order that the electronic image picked up by each ophthalmologic apparatus is captured, an image processing apparatus specialized to each ophthalmologic apparatus is required.

If a single image processing apparatus is used for all ophthalmologic apparatuses, a problem in which the operator needs to set necessary image processing for each ophthalmologic apparatus is caused. In addition, a fear that erroneous setting is performed by the operator cannot be eliminated.

Also, when the FAG image pickup is performed, the operator should perform operations such as conversion of color information into white-and-black information, setting of the γ characteristic, and contrast enhancement with respect to the picked up color electronic image using the image processing apparatus. Therefore, operation efficiency is low. Even in the ICG image pickup, operations other than the color information conversion are performed as in the FAG image pickup.

SUMMARY OF THE INVENTION

The present invention has been made to solve the above-mentioned problems and accordingly, an object of the present invention is to provide an ophthalmologic image pickup system capable of processing information obtained by a plurality of image pickup devices by using a single processing apparatus.

In order to achieve the above-mentioned object, an ophthalmologic image pickup system according to the present invention includes: a plurality of image pickup devices, each of which has image data generating means for picking up an image of an eye to be examined to generate image data; device information determination means for determining inputted device information related to the image pickup devices; and image processing means for performing different image processings on the image data in accordance with a result of the device information determination means.

DESCRIPTION OF THE PREFERRED EMBODIMENTS

The present invention will be described in detail with reference to embodiments shown in the drawings.

Figure 1:
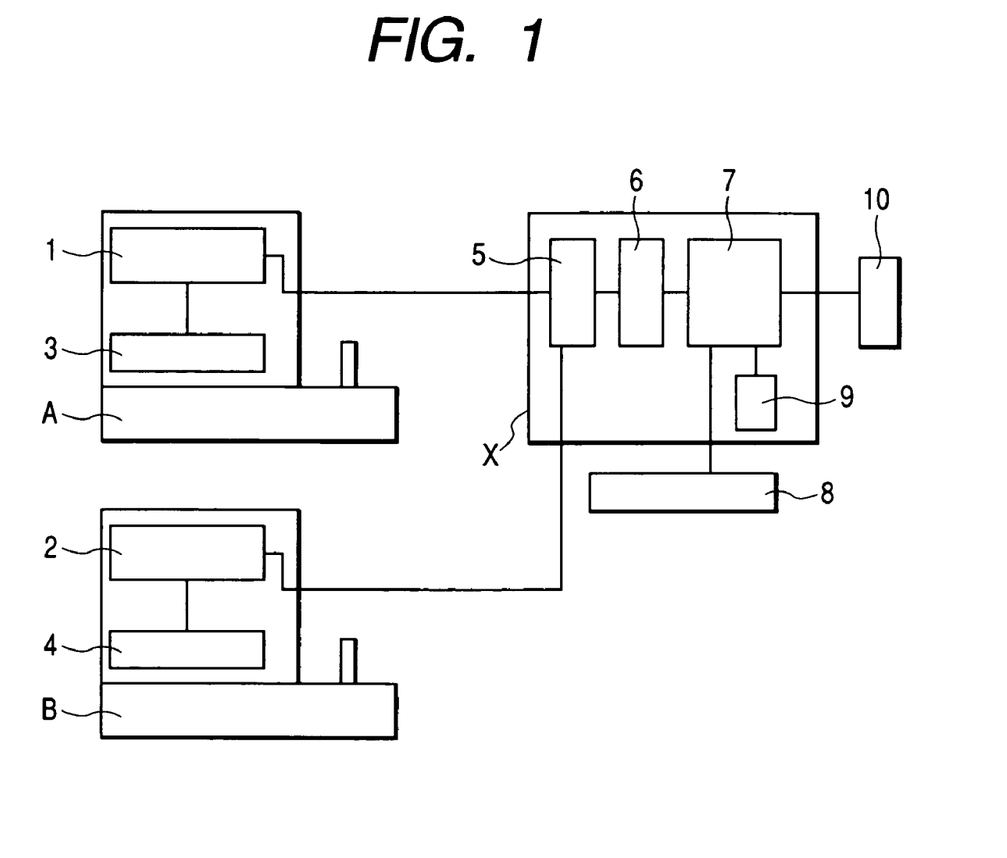
FIG. 1 is a structural diagram showing an embodiment in which the present invention is applied to an eye fundus camera.

In FIG. 1, outputs of digital eye fundus cameras A and B are connected with an image processing apparatus X. The eye fundus camera A includes an image data generation unit 1 and a device information generation unit 3. The eye fundus camera B includes an image data generation unit 2 and a device information generation unit 4. The image data generation units 1 and 2 each pick up an eye fundus image of an eye to be examined and generate an eye fundus image as image data. The device information generation units 3 and 4 each generate information related to a device (eye fundus camera) that has performed image pickup and add the information to the generated eye fundus image. The common image processing apparatus X is provided for the eye fundus cameras A and B. Outputs of the image data generation units 1 and 2 of the eye fundus cameras A and B are connected with a device information determination unit 5 of the image processing apparatus X. An output of the device information determination unit 5 is connected with a control unit 7 through an image processing unit 6. The control unit 7 is connected with a patient information input unit 8, a memory unit 9, and a monitor 10.

Figure 2:
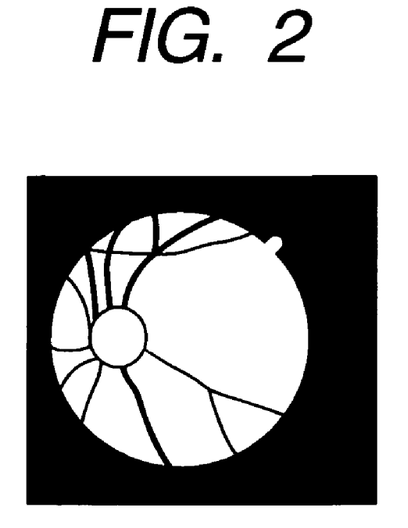
FIG. 2 is an explanatory view showing an image picked up by an eye fundus camera A.

For example, when an image of the left eye of a subject is picked up, the eye fundus image which is the image data generated by the eye fundus camera A is as shown in FIG. 2 in a stage in which the eye fundus image has been transmitted to the image processing apparatus X. That is, an aperture mask indicating an image pickup area is provided in the eye fundus camera A (in the device). Note that the top, the bottom, the right, and the left of the eye fundus region are picked up as in a conventional case.

Figure 3:
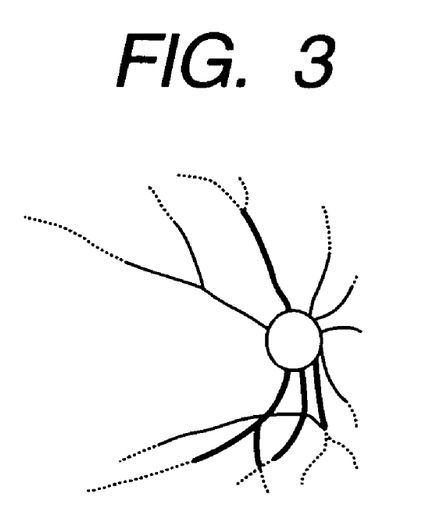
FIG. 3 is an explanatory view showing an image picked up by an eye fundus camera B.

On the other hand, the aperture mask is not provided in the eye fundus camera B (in the device). In addition to this, because the eye fundus image is formed on an image pickup device in a vertically and horizontally reversed state with respect to the case of the eye fundus camera A, even when an image of the same eye fundus is picked up, image data in which the aperture mask indicating the image pickup area does not exist is obtained as shown in FIG. 3.

Figure 4:
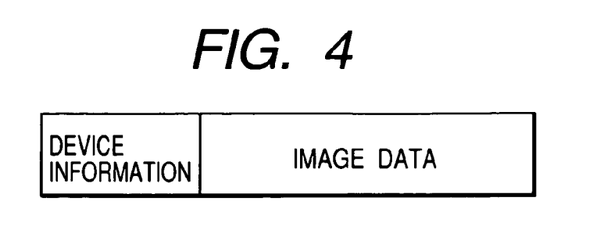
FIG. 4 is an explanatory view showing data to be transmitted.

Also, the device information generation units 3 and 4 each generate device information for specifying which processing should be performed on the eye fundus image and transmit the image data to which the device information is added as shown in FIG. 4 to the image processing apparatus X.

Here, the device information data generated by each of the device information generation units 3 and 4 includes "T O P Q R". More specifically, codes of processings O and P related to reverse processing of the image, a code of processing Q related to the aperture mask, and a code of processing R related to an image pickup mode follow an identification code T indicating the presence of information related to processing, and are defined as shown in Table 1.

TABLE 1

| Processing | Numerical value 0 | Numerical value 1 | Numerical value 2 |
|---|---|---|---|
| O | Image horizontal reverse not needed | Image horizontal reverse executed | |
| P | Vertical reverse not needed | Vertical reverse executed | |
| Q | Aperture mask synthesization not needed | Aperture mask additional synthesization executed | |
| R | Color image | FAG image | ICG image |

According to the processing R, any processing is not performed in the case of a color image. In the case of an FAG image, while considering ease of diagnosis, it is converted into a white-and-black image, and γ characteristic adjustment and contrast processing are performed thereon. In addition, even in the case of an ICG image, it is considered to perform the γ characteristic adjustment, the contrast processing, and the like.

Next, operations will be described according to an operation flow of a flow chart of FIG. 5. First, it is considered that the FAG image pickup is performed using the eye fundus camera A. In Step S1, patient information such as a patient ID number of a subject, a name thereof, a birth date thereof, or a sex thereof is inputted from the patient information input unit 8 to the control unit 7 of the image processing apparatus X before image pickup by a person that performs image pickup.

In Step S2, an image of the eye fundus of the eye to be examined is picked up using the image data generation unit 1 of the eye fundus camera A. In Steps S3 and S4, the image data generation unit 1 adds onto the image data the device information generated by the device information generation unit 3 connected therewith as additional information. In this case, the device information becomes "T 0 0 0 1" because the eye fundus camera A is used.

In Step S5, the image data to which the device information is added is inputted to the device information determination unit 5 of the image processing apparatus X. In Step S6, the device information is read out from the inputted image data by the device information determination unit 5 and processing required for the image data is determined thereby.

In Step S7, processing is selected based on the determination result.

In this case, the device information is "T 0 0 0 1". Therefore, in the image processing unit 6, the horizontal reverse and the vertical reverse are not performed and it is unnecessary to synthesize the aperture mask. However, because of the FAG image pickup, in Step S8, the color image is converted into the white-and-black image, the γ characteristic is adjusted, and the contrast processing is performed.

Figure 6A:
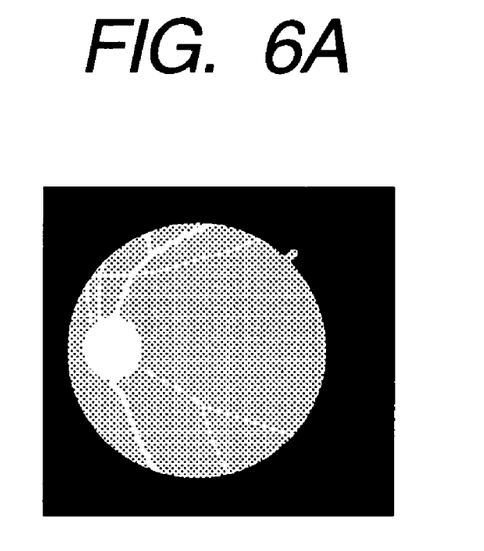
FIGS. 6A and 6B are explanatory views each showing processing of the image picked up by the eye fundus camera A.
Figure 6B:
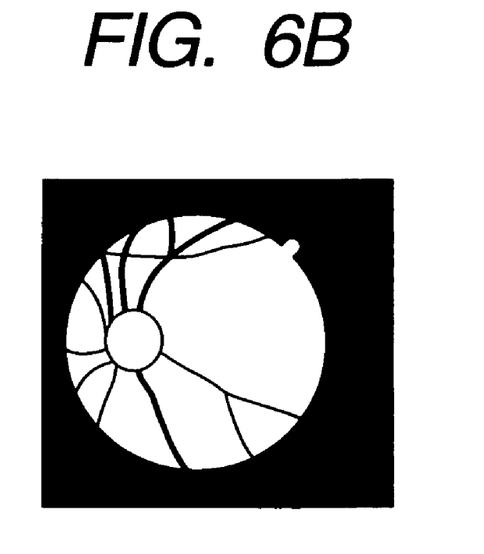

FIG. 6A shows the image transmitted from the eye fundus camera A and FIG. 6B shows the image processed by the image processing unit 6. Note that it is originally considered in FIG. 6B that a blood vessel is displayed in white and an eye fundus segment is displayed in gray. However, they are reversely shown in FIG. 6B to easily understand a change. In Step S7, the image data processed by the image processing unit 6 is transmitted to the control unit 7, and then stored in relation to the patient information such as the patient ID number in the memory unit 9 and displayed on the monitor 10 if necessary.

Figure 5:
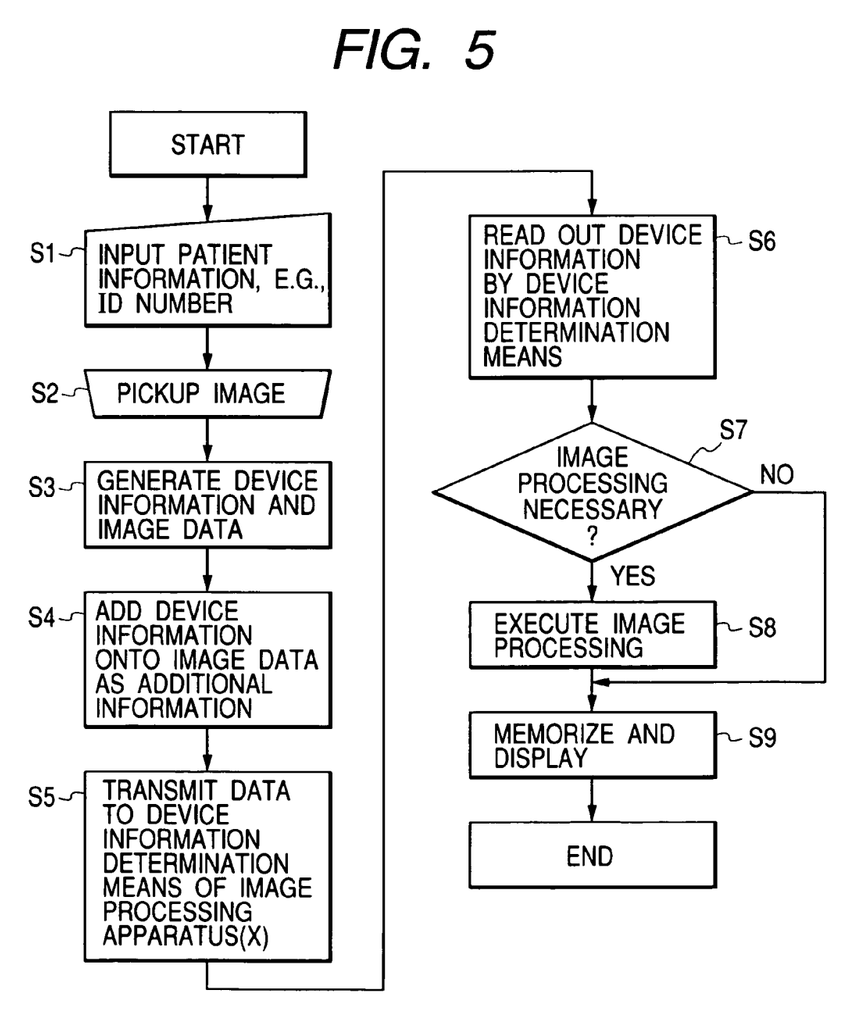
FIG. 5 is a flow chart showing image processing.

In the case of color image pickup using the eye fundus camera B, after Step S1 in FIG. 5, the color image pickup is performed by the image data generation unit 2 of the eye fundus camera B in Step S2. In Steps S3 and S4, device information "T 1 1 1 0" is generated by the device information generation unit 4 and added to image data.

The image data is transmitted in Step S5. After that, in Step S6, device information is read out by the device information determination unit 5 and adequate processing is performed on the transmitted image data thereby.

In this case, because the device information is "T 1 1 1 0", Step S8 is selected in Step S7. Therefore, in the image processing unit 6, the horizontal reverse and the vertical reverse are performed and the aperture mask is synthesized. However, the γ characteristic adjustment and the like are not performed because of the color image pickup.

Figure 7A:
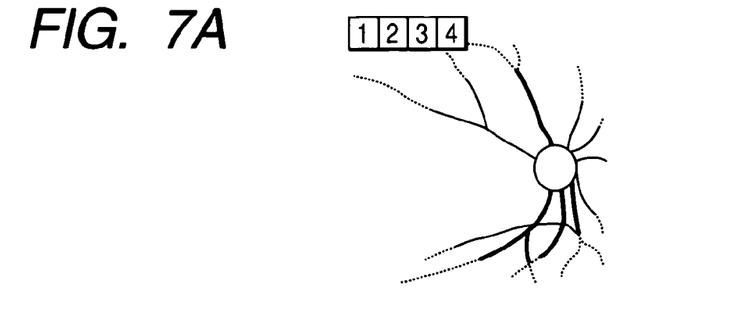
FIGS. 7A, 7B, 7C and 7D are explanatory views each showing processing of the image picked up by the eye fundus camera B.
Figure 7B:
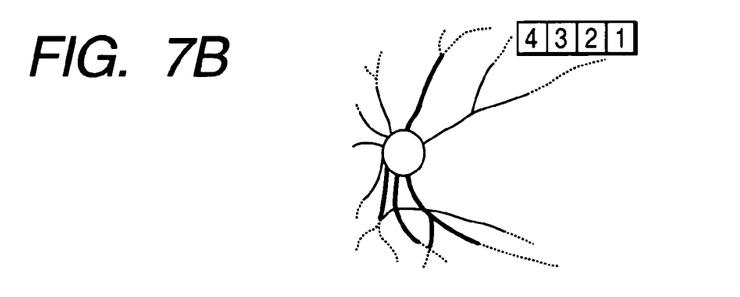

FIG. 7A shows the image which is transmitted from the eye fundus camera B and overlapped with addresses 1, 2, 3, 4, . . . for explanation. FIG. 7B shows the image which is horizontally reversed by the image processing unit 6. In the reverse processing, only the arrangement may be reversed without changing rows of addresses.

Figure 7C:
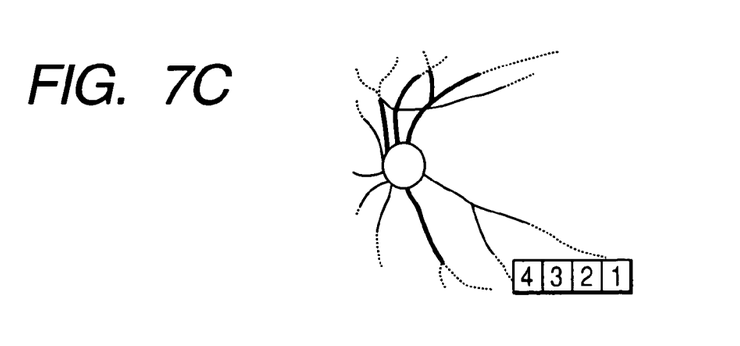
Figure 7D:
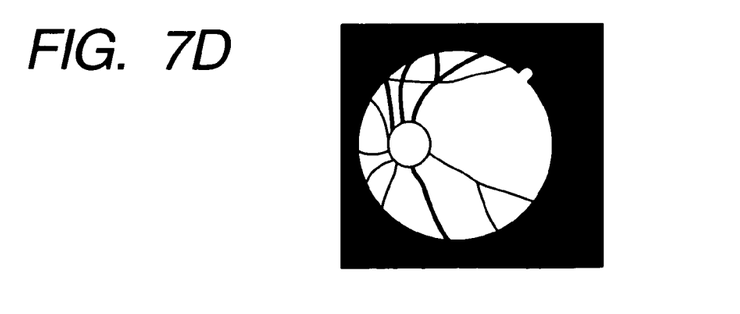

Subsequently, vertical reverse processing is performed. As shown in FIG. 7C, the horizontally reversed image may be located such that a first row address thereof becomes a final row. Further, the image is electronically synthesized with an aperture mask, thereby obtaining the image as shown in FIG. 7D. Finally, as in the above-mentioned case, after the image shown in FIG. 7D is transmitted to the control unit 7 in Step S8, in Step S9, the image is stored in relation to the patient information such as the patient ID number in the memory unit 9 and displayed on the monitor 10 if necessary.

Also, it is possible that the system is specialized to processing on the image data according to the image pickup mode as follows: an image pickup information generation unit that generates information related to an image pickup mode is used instead of the device information generation unit described in this embodiment and the device information determination unit 5 is replaced by an image pickup information determination unit.

Further, the horizontal reverse processing and the vertical reverse processing are separately performed in this embodiment. However, because it is determined whether or not the two processings are performed at a time when the device information is read, it is needless to say that the processings may be performed at the same time.

Figure 8:
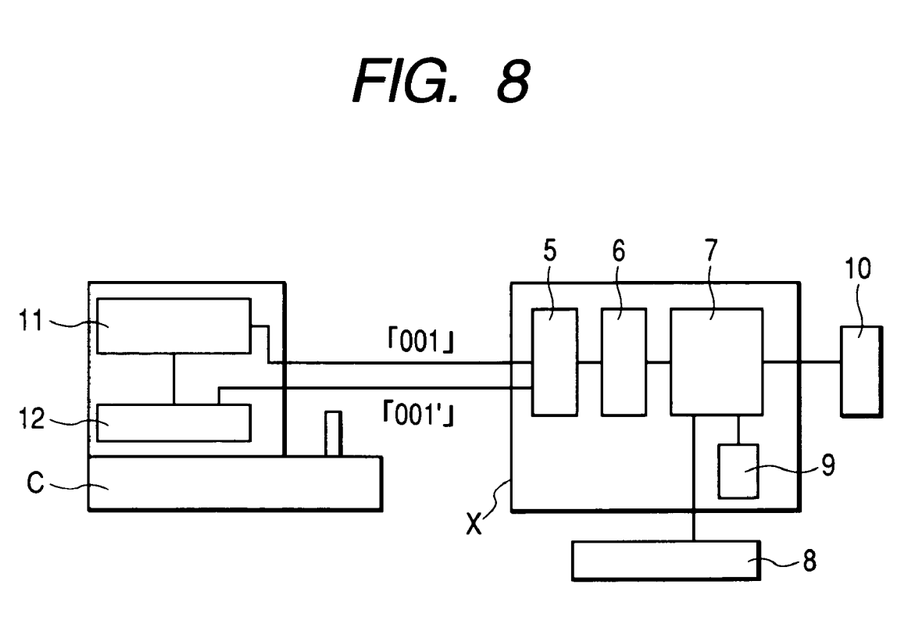
FIG. 8 is a structural diagram showing another embodiment of the present invention.

Also, in this embodiment, the image data to which the device information is added as tag information is transmitted to the image processing apparatus X. In addition to this, it is considered that the image data is transmitted using, for example, serial communication or parallel communication. As shown in FIG. 8, in this case, an image data generation unit 11 and a device information generation unit 12 are provided in an eye fundus camera C and the image processing apparatus X has the same structure as shown in FIG. 1.

The image data "001" picked up by the image data generation unit 11 is transmitted to the image processing unit 6 through the device information determination unit 5 of the image processing apparatus X using, for example, a USB or an IEEE1394. In addition, the device information "001'"corresponding to the image data "001" is generated by the device information generation unit 12 and transmitted to the device information determination unit 5 using, for example, an RS232C in the case of serial communication or a PC-bus in the case of parallel communication. A content of the device information "001'" is based on a format described earlier in Table 1: first data (code) T corresponds to a command indicating the device information and the following correspond to the content.

The image processing unit 6 processes the image data according to the result of the device information determination unit 5. After that, the image data is stored in relation to the patient information such as the patient ID number in the memory unit 9.

Further, with respect to another embodiment, "TS" is used as the information generated by the device information generation unit 12. That is, only a content which can specify the apparatus is used as shown in Table 2 below.

TABLE 2

| S | Numerical value 0 | Numerical value 1 | Numerical value 2 |
|---|---|---|---|
| | Eye fundus camera A | Eye fundus camera B | Eye fundus camera C |

On the other hand, when the image processing apparatus X has an image processing table corresponding to a processing content of the image data as shown in Table 3 below, the same effect can be obtained.

TABLE 3

| | Processing content |
|---|---|
| Eye fundus camera A | no processing |
| Eye fundus camera B | Horizontal reverse and vertical reverse, and electronic mask synthesization |
| Eye fundus camera C | Vertical reverse |

Alternatively, as shown in Table 4, it is considered that "T S U" is used as device information and the device information is transmitted to the image pickup mode generation unit 11.

TABLE 4

| | Numerical value 0 | Numerical value 1 | Numerical value 2 |
|---|---|---|---|
| S | Eye fundus camera A | Eye fundus camera B | Eye fundus camera C |
| V | Color image | FAG image | ICG image |

Note that the device information in Table 4 includes detail processing settings as shown in Table 5 below.

TABLE 5

Eye fundus camera A

Color image → No image processing
FAG image → White-and-black conversion, $\gamma$ value = 0.45, Contrast = 65
ICG image → Contrast = 75
Eye fundus camera B Color image → No image processing
FAG image → White-and-black conversion, $\gamma$ value = 0.48, Contrast = 60
ICG image → $\gamma$ value = 0.46, Contrast = 75
Eye fundus camera C Color image → No image processing
FAG image → White-and-black conversion, $\gamma$ value = 0.43, Contrast = 68
ICG image → $\gamma$ value = 0.49, Contrast = 75

Therefore, for example, even in processing related to the same FAG image pickup, the extent of the $\gamma$ characteristic adjustment, the contrast processing, and the like can be set in detail for each image pickup device.

Also, in the above-mentioned embodiment, the device is constructed that the device information or the image pickup information is generated therein. It is also conceivable that the information is directly inputted by an examiner.

Here, aspects of the present invention are described below. One aspect of the present invention relates to an ophthalmologic image pickup system, including: a plurality of image pickup devices, each of which has image data generating means for picking up an image of an eye to be examined to generate image data; device information determination means for determining inputted device information related to the image pickup devices; and image processing means for performing different image processings on the image data in accordance with a result of the device information determination means.

In the image pickup system, preferably, the image pickup device information includes information related to at least one of processing for vertically reversing the image data and processing for horizontally reversing the image data.

According to the aspects, when an image pickup device is designed, it is unnecessary to take into consideration the number of imaging of an image and the number of reflection by mirrors. Therefore, the flexibility in design is improved and cost reduction can be achieved.

Also, in the ophthalmologic image pickup system, preferably, the image pickup device information includes information related to synthesis of the image data with an electronic aperture mask.

According to this aspect, the aperture mask is not necessarily provided in the image pickup device. Therefore, cost reduction can be achieved.

Further, another aspect of the present invention relates to an ophthalmologic image pickup system, including: a plurality of image pickup devices having image data generation means, each of which picks up an image of an eye to be examined to generate image data thereof; device information determination means for determining inputted device information related to the image pickup device; a processing table in which the corresponding image pickup device and an image data processing method therefor are shown; and image processing means for performing different image processings on the image data in accordance with a determination result of the device information determination means and the processing table.

According to this aspect, it is unnecessary to use an image processing apparatus that captures image data for each image pickup device and performs image processing thereon. That is, the plurality of image pickup devices can be treated by the single image processing apparatus, thereby achieving cost reduction. In addition, it is unnecessary to take into account a kind of device, so that an error is prevented and the operation is easy. When the image pickup device is designed, it can be designed without considering an output image of the image data, so that the degree of freedom of the design is increased. In addition, when a new image pickup device is used, it is necessary to merely update the processing table.

Further, in the ophthalmologic image pickup system, preferably, the device information includes a description of a kind of the image pickup device.

According to this aspect, the device information can be simplified.

Further, in the ophthalmologic image pickup system, preferably, the processing method shown in the processing table relates to at least one of processing for horizontally reversing the image data and processing for vertically reversing the image data.

According to this aspect, when the image pickup device is designed, it is unnecessary to take into account the number of imaging of the image and the number of reflection by mirrors. Therefore, the degree of freedom of the design is improved and cost reduction can be achieved.

Further, in the ophthalmologic image pickup system, preferably, the processing method shown in the processing table is to synthesize an electric aperture mask with the image data.

According to this aspect, when the image pickup device is designed, it is unnecessary to take into account the number of imaging of the image and the number of reflection by mirrors. Therefore, the degree of freedom of the design is improved and cost reduction can be achieved.

In the ophthalmologic image pickup system according to any one of the aspects of the invention, preferably, the image pickup device includes device information generation means for generating device information, the device information generation means is connected with the image data generation means, and the image data generation means adds the device information generated by the device information generation means to the image data and inputs the image data to which the device information is added to the device information determination means.

According to this aspect, the number of cables provided between the image pickup device and the image processing apparatus can be reduced and a general-purpose format related to the image data can be utilized as it is. In addition, erroneous processing based on erroneous input can be prevented.

In the ophthalmologic image pickup system according to any one of the aspects of the invention, preferably, the image pickup device includes device information generation means for generating device information, and the image data and the device information are separately inputted to the device information determination means.

According to this aspect, it is unnecessary to provide a unit that describes information in a tab of the image, so that the device information can be relatively easily transmitted using a command.

Further, another aspect of the present invention relates to an ophthalmologic image pickup system, including: an image pickup device including image data generation means for picking up an image of an eye to be examined to generate image data thereof; and image pickup information determination means for determining inputted image pickup information; and image processing means for performing different image processings on the image data in accordance with a result of the image pickup information determination means.

According to this aspect, complicated procedure of performing image processing on the image data after the completion of the image pickup is unnecessary, which is time-saving.

In the ophthalmologic image pickup system, preferably, the image pickup device further includes image pickup information generation means for generating image pickup information related to an image pickup mode upon image pickup, the image pickup information generation means is connected with the image data generation means, and the image data generation means adds the image pickup information generated by the image pickup information generation means to the image data and inputs the image data to which the image pickup information is added to the image pickup information determination means.

According to this aspect, based on the three image pickup modes, no special processing is separately performed or such processing can be performed.

Further, in the ophthalmologic image pickup system, preferably, the image pickup mode is one of a color image pickup mode, a visible Fluorescein fundus angiography mode, and an Indocyanine green angiography mode.

According to this aspect, it is unnecessary for an operator to perform the operations such as the conversion of color information into white-and-black information, setting of the γ characteristic, and the contrast processing with respect to the picked up visible fluorescence electronic image using the image processing apparatus.

In the ophthalmologic image pickup system, preferably, the different image processings include at least one of conversion of the image data into a white-and-black image, γ characteristic adjustment thereof, and contrast processing thereof when the image pickup mode is one of the Fluorescein fundus angiography mode and the Indocyanine green angiography mode.

According to this aspect, the number of cables provided between the image pickup device and the image processing apparatus can be reduced and the general-purpose format related to the image data can be utilized as it is. In addition, erroneous processing based on erroneous input can be prevented.

In the ophthalmologic image pickup system, preferably, the image pickup device further includes image pickup information generation means for generating image pickup information related to an image pickup mode upon image pickup, and the image data and the image pickup information are separately inputted to the image pickup information determination means.

According to this aspect, it is unnecessary to provide a unit that describes information in a tab of the image, so that the device information can be relatively easily transmitted using a command.

Also, in the above-mentioned system, it is preferable that different image processing to the image data differs according to the image pickup device that has performed the image pickup.

According to this aspect, even in processing related to the same FAG image pickup, the extent of the γ characteristic adjustment, the contrast processing, and the like can be set in detail for each image pickup device.

As described above, in the ophthalmologic image pickup system according to the present invention, it is unnecessary to use the image processing apparatus that captures the image data for each image pickup device and performs image processing thereon. The plurality of image pickup devices can be treated by the single image processing apparatus, whereby cost reduction is achieved. In addition, it is unnecessary to take into account a kind of device, so that an error is prevented and the operation is easy. When the image pickup device is designed, it can be designed without considering an output image of the image data, so that the degree of freedom of the design is increased.

What is claimed is:

1. An ophthalmologic image pickup system, comprising:
an image pickup device having;
an output unit for adding an image pickup device information to an image data of eye fundus which is picked up by the image pickup device, and outputting the image data to an image processing device; and
the image processing device having;
a determination unit for determining an image processing to be performed based on the image pickup device information added to the image data which is outputted from the output unit; and
an image processing unit for performing the image processing on the image data to which the image pickup device information is added, in accordance with a determination result of the determination unit,
wherein the image processing device is connectable with a plurality of image pickup devices which pickup deferent image data to be performed different image processings,
wherein, in a case that the determination unit determines different image processing on each of image data picked up by the image pickup devices, the image processing unit performs different image processing corresponding to each image pickup device information,
wherein the determination unit determines the image processing to be performed in accordance with a processing table showing an image data processing method corresponding to the image pickup device information.

2. An ophthalmologic image pickup system according to claim 1, wherein the image pickup device information includes information indicating whether or not at least one of processing for vertically reversing the image data and processing for horizontally reversing the image data should be performed by the image processing unit.

3. An ophthalmologic image pickup system according to claim 1, wherein the image pickup device information includes information indicating whether or not the image data should be synthesized with an electronic aperture mask by the image processing unit.

4. An ophthalmologic image pickup system according to claim 1, wherein the image pickup device information includes a kind of the image pickup device.

5. An ophthalmologic image pickup system according to claim 1, wherein the image pickup device information includes information regarding an image pickup mode of one of a color image pickup mode, a Fluorescein fundus angiography mode, and an Indocyanine green angiography mode.

6. An ophthalmologic image pickup system according to claim 1, wherein the image processing unit performs at least one of conversion of the image data into a white-and-black image, γ characteristic adjustment thereof, and contrast processing thereof when information regarding an image pickup mode is one of a Fluorescein fundus angiography mode and an Indocyanine green angiography mode.

7. An image processing device of an ophthalmologic image pickup system, comprising:
a determination unit for determining an image processing to be performed based on an image pickup device information added to an image data of eye fundus which is picked up by an image pickup device and outputted from an output unit; and
an image processing unit for performing the image processing on the image data, to which the image pickup device information is added, in accordance with a determination result of the determination unit,
wherein the ophthalmologic image pickup system has an image pickup device that has the output unit for adding the image pickup device information to the image data of eye fundus which is picked up, and for outputting the image data to the image processing device,
wherein the image processing device is connectable with a plurality of image pickup devices which pickup deferent image data to be performed different image processings,
wherein, in a case that the determination unit determines different image processing on each of image data picked up by the image pickup devices, the image processing unit performs different image processing corresponding to each image pickup device information,
wherein the determination unit determines the image processing to be performed in accordance with a processing table showing an image data processing method corresponding to the image pickup device information.

8. An image pickup device of an ophthalmologic image pickup system, comprising:
an output unit for adding an image pickup device information to an image data of eye fundus which is picked up by the image pickup device, and for outputting the image data to an image processing apparatus;
the image processing device has;
a determination unit for determining an image processing to be performed based on the image pickup device information added to the image data which is outputted from the output unit; and an image processing unit for performing the image processing on the image data, to which the image pickup device information is added, in accordance with a determination result of the determination unit, wherein the image processing device is connectable with a plurality of image pickup devices which pickup deferent image data to be performed different image processings, wherein, in a case that the determination unit determines different image processing on each of image data picked up by the image pickup devices, the image processing unit performs different image processing corresponding to each image pickup device information, and wherein the determination unit determines the image processing to be performed in accordance with a processing table showing an image data processing method corresponding to the image pickup device information.

* * * * *